United States Patent [19]
Tsonton et al.

[11] Patent Number: 5,944,737
[45] Date of Patent: Aug. 31, 1999

[54] ULTRASONIC CLAMP COAGULATOR APPARATUS HAVING IMPROVED WAVEGUIDE SUPPORT MEMBER

[75] Inventors: Mark Tsonton, Cincinnati, Ohio; Stephen DiMatteo, Plymouth, Mass.

[73] Assignee: Ethicon Endo-Surgery, Inc., Cincinnati, Ohio

[21] Appl. No.: 08/949,161

[22] Filed: Oct. 10, 1997

[51] Int. Cl.[6] .................................................. A61B 17/28
[52] U.S. Cl. ............................ 606/205; 606/169; 604/22
[58] Field of Search ..................................... 606/205, 107, 606/151, 157, 167, 170, 171, 144, 169; 601/2; 604/22–24

[56] References Cited

U.S. PATENT DOCUMENTS

| | | |
|---|---|---|
| Re. 30,536 | 3/1981 | Perdreaux, Jr. . |
| 2,874,470 | 2/1959 | Richards . |
| 3,076,904 | 2/1963 | Kleesatel et al. . |
| 3,368,280 | 2/1968 | Freidman et al. . |
| 3,488,851 | 1/1970 | Haydu . |
| 4,370,131 | 1/1983 | Banko . |
| 4,522,206 | 6/1985 | Whipple et al. . |
| 4,750,488 | 6/1988 | Wuchinich et al. . |
| 5,322,055 | 6/1994 | Davison et al. ........................ 606/169 |
| 5,346,502 | 9/1994 | Estabrook et al. . |

FOREIGN PATENT DOCUMENTS

| | | | |
|---|---|---|---|
| 8-275948 | 10/1996 | Japan ..................................... 606/169 |
| 8-275949 | 10/1996 | Japan . |
| 8-275951 | 10/1996 | Japan . |
| 9-98980 | 4/1997 | Japan . |
| WO 93/14708 | 8/1993 | WIPO ..................................... 606/169 |
| WO93/14708 | 8/1993 | WIPO . |

OTHER PUBLICATIONS

UltraCision Incorporated, Harmonic Scalpel Operating Manual, Ref. N Mar. 1995, 53 pages.
UltraCision Incorporated, Harmonic Scalpel Price List, Jul. 1995, 7 pages.
UltraCision Incorporated, The Harmonic Scalpel for Gynecological Surgery, 1993, 4 pages.
UltraCision CS/LS Layout, Jul. 24, 1995, 2 pages.
Snowden–Spencer, Inc., Endoscopic Plastic Surgery, 1993, 10 pages.

*Primary Examiner*—Michael Buiz
*Assistant Examiner*—Lien Ngo
*Attorney, Agent, or Firm*—Bernard Shay

[57] ABSTRACT

An ultrasonic surgical clamp coagulator apparatus is configured to effect cutting, coagulation, and clamping of tissue by cooperation of a clamping mechanism of the apparatus with an associated ultrasonic end-effector. The ultrasonic waveguide of the apparatus is preferably provided with an improved support member at the distal-most node thereof, which support member desirably functions to resist bending moments created in the waveguide, attendant to operation of the clamping mechanism, while sealing the region adjacent to the waveguide.

14 Claims, 7 Drawing Sheets

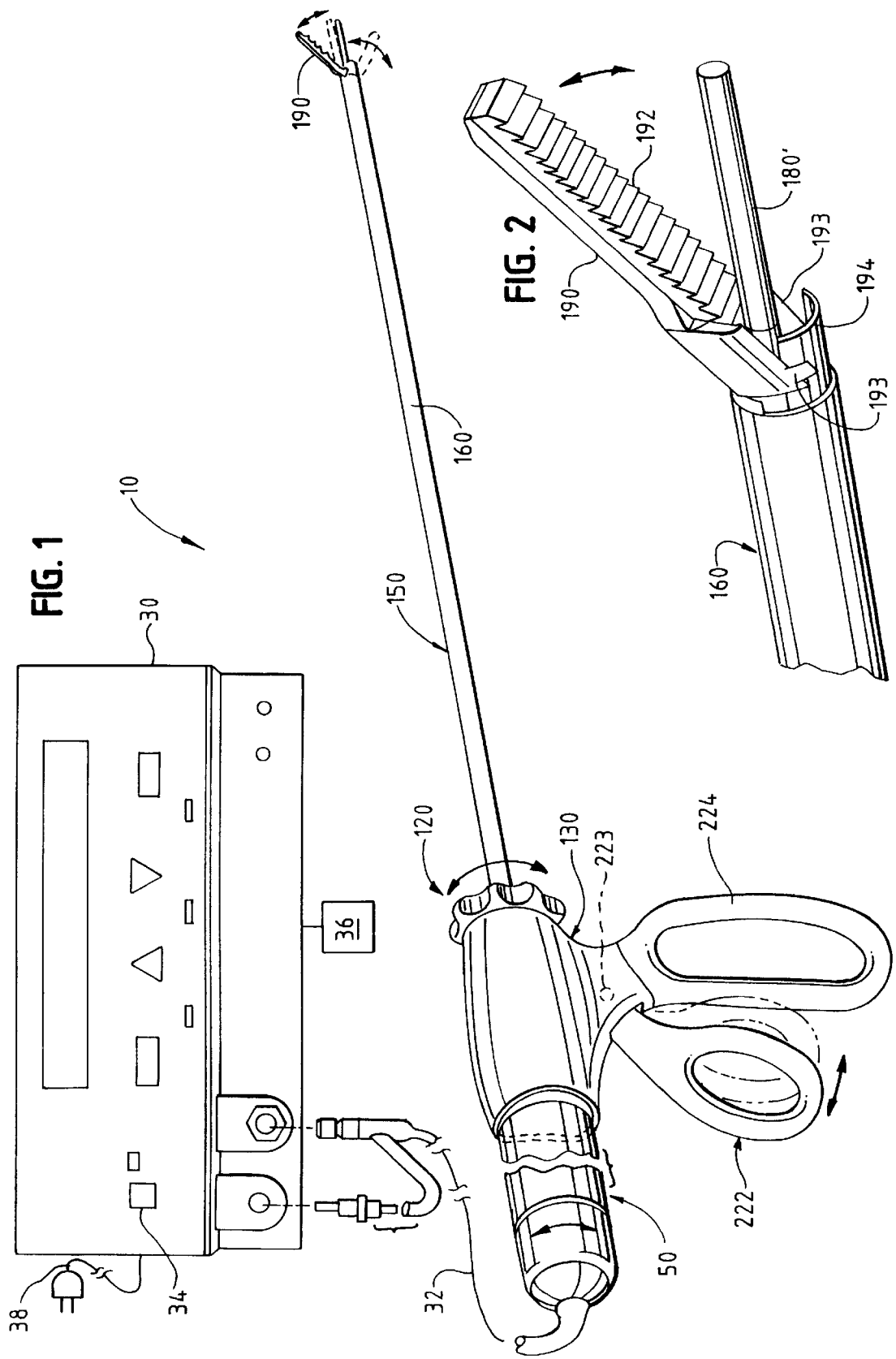

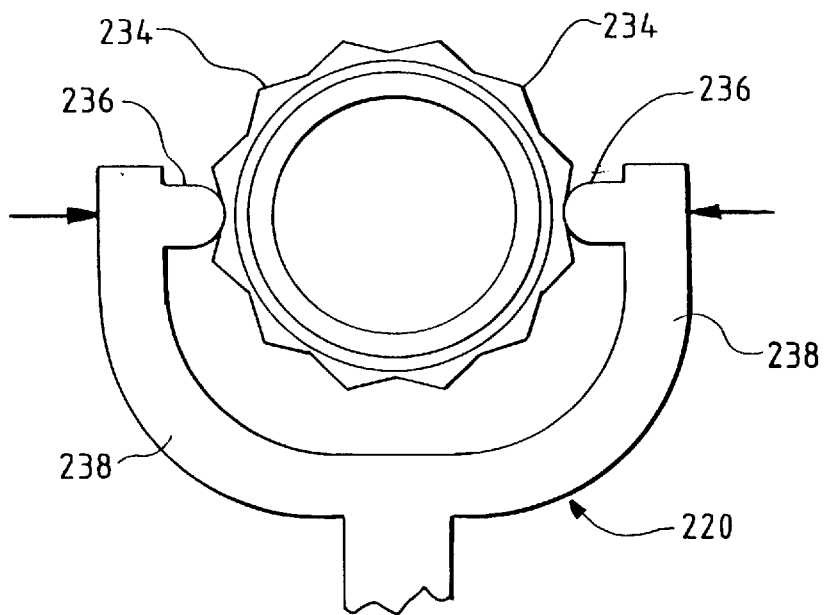
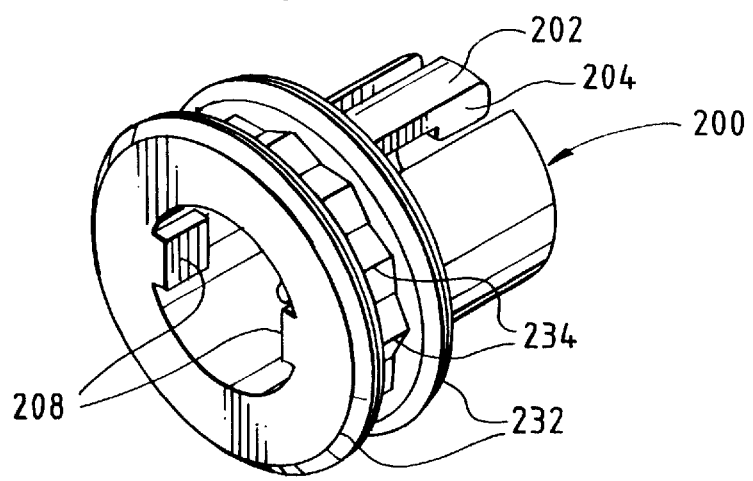

ULTRASONIC CLAMP COAGULATOR APPARATUS HAVING IMPROVED WAVEGUIDE SUPPORT MEMBER

TECHNICAL FIELD

The present invention relates generally to ultrasonic surgical devices, and more particularly to an ultrasonic surgical clamp coagulator apparatus for coagulating and/or cutting tissue, including an improved thin-walled support and sealing member for the ultrasonic waveguide of the apparatus which resists bending moments created during clamping of tissue against an end-effector of the waveguide.

BACKGROUND OF THE INVENTION

Ultrasonic surgical instruments are finding increasingly widespread applications in surgical procedures by virtue of the unique performance characteristics of such instruments. Depending upon specific instrument configurations and operational parameters, ultrasonic surgical instruments can provide substantially simultaneous cutting of tissue and hemostasis by coagulation, desirably minimizing patient trauma. The cutting action is typically effected by an end-effector at the distal end of the instrument, with the end-effector transmitting ultrasonic energy to tissue brought into contact therewith. Ultrasonic instruments of this nature can be configured for open surgical use, or laparoscopic or endoscopic surgical procedures.

Ultrasonic surgical instruments have been developed that include a clamp mechanism to press tissue against the end-effector of the instrument in order to couple ultrasonic energy to the tissue of a patient. Such an arrangement (sometimes referred to as an ultrasonic transector) is disclosed in U.S. Pat. No. 5,322,055, hereby incorporated by reference.

In previous ultrasonic instruments, the waveguide of the instrument, through which ultrasonic energy is directed, is typically provided with one or more ring-like members for acoustically dampening the waveguide, and isolating the waveguide from surrounding components. Such isolation members are typically provided at one or more nodes of longitudinal vibration of the waveguide, and are typically constructed of elastomeric material, such as silicone rubber. Isolation members of this type desirably prevent loss of vibrational energy from the waveguide which can occur under side-loading or bending conditions which might otherwise cause indirect contact of the waveguide with an associated component positioned thereabout.

In ultrasonic surgical instruments heretofore known for endoscopic applications, the outside diameter of the elongated endoscopic portion of such instruments has been on the order of 10 mm. As such, it is ordinarily been possible to provide suitable isolation members for the waveguide of such instruments, while still providing a waveguide having a sufficiently large cross-section for the desired rigidity and for delivery of the desired level of ultrasonic energy without excessive heating of the waveguide.

Continued development of ultrasonic surgical instruments has desirably resulted in instruments having even smaller endoscopic portions, on the order of 6 mm in diameter or less. When configuring ultrasonic instruments of this relatively small size, it is important that the desired acoustic dampening of the waveguide be effected, while still providing the waveguide with a cross-section which is as large as practicable. Problems in isolating the waveguide can be particularly exacerbated in ultrasonic instruments configured to effect clamping of tissue against an end-effector of the instrument, since such clamping creates bending moments within the waveguide flexing the waveguide from its normal, unloaded configuration.

The present invention is directed to an improved support member for an ultrasonic surgical instrument, with the support member of the present invention particularly suited for use in instruments configured for endoscopic applications having relatively small cross-sections.

SUMMARY OF THE INVENTION

In accordance with the present invention, an ultrasonic surgical clamp coagulator apparatus is configured to permit selective cutting, coagulation, and clamping of tissue during surgical procedures. In order to acoustically dampen the waveguide of the apparatus, the apparatus includes an annular support member positioned at the distal-most node of the waveguide. The annular support member is configured to include a support portion which acts to isolate the waveguide from surrounding components, and a sealing portion which effects sealing between the waveguide and a reciprocable tubular actuating member positioned around the waveguide. By this construction, the annular support member dampens unwanted modes of vibration while allowing desired modes of vibration, effects sealing of the region about the waveguide, and maximizes the cross-sectional area available for the active waveguide within the elongated tubular portion of the instrument.

In accordance with the illustrated embodiment, the present ultrasonic surgical clamp apparatus includes a housing, and an outer tubular sheath having a proximal end joined to the housing. An inner tubular actuating member is reciprocably positioned within the outer tubular sheath, and is operatively connected to a clamp arm pivotally mounted on a distal end of the outer tubular sheath. The clamp arm is mounted for pivotal movement with respect to an end-effector of an ultrasonic waveguide positioned within the inner tubular actuating member. In the illustrated embodiment, the outer tubular sheath, the inner tubular actuating member, and the ultrasonic waveguide are mounted for rotation together with respect to the apparatus housing, with the actuating member being reciprocable with respect to both the outer tubular sheath as well as the ultrasonic waveguide positioned within the actuating member. Reciprocable movement of the actuating member pivotally moves the clamp arm with respect to the end-effector of the waveguide.

In accordance with the present invention, an annular support member is mounted on the waveguide at a distal-most node thereof. The support member preferably comprises elastomeric material, such as silicone rubber, and is configured to provide a combination of functions for enhancing the performance of the apparatus. Specifically, the support member includes a support portion having a generally cylindrical outer support surface which is positioned between the waveguide and the actuating member for resisting bending moments created during clamping of tissue against the end-effector by the pivotal clamp arm. The support member further includes a sealing portion for sealing the region between the waveguide and the relatively reciprocable actuating member. In the preferred embodiment, the sealing portion has a pair of converging surfaces which converge and meet each other to define a peripheral sealing region spaced radially outwardly of the outer cylindrical support surface of the support portion of the member.

In accordance with illustrated embodiments of the invention, the sealing portion of the support member is spaced axially from the support portion thereof, either distally or proximally. In alternate embodiments, the sealing portion of the support member is positioned medially of the support portion. For each of the various embodiments of the support member, the associated waveguide can be configured to include a lug portion having a diameter greater than the portions of the waveguide adjacent thereto. The support member of the present invention is preferably positioned with respect to such a lug portion so that this support portion of the support member is positioned on and flanks the lug portion of the waveguide. In those embodiments of the present support member wherein the sealing portion is positioned medially of the support portion, the sealing portion can be positioned in substantial alignment with the lug portion of the waveguide.

Other features and advantages of the present invention will become readily apparent from the following detailed description, the accompanying drawings, and the appended claims.

BRIEF DESCRIPTION OF THE DRAWINGS

FIG. 1 is a perspective view of an ultrasonic surgical system including an ultrasonic clamp coagulator apparatus embodying the principles of the present invention;

FIG 2 is an enlarged, fragmentary perspective view of a clamp mechanism of the clamp coagulator apparatus illustrated in FIG. 1;

FIG. 7 is a diagrammatic view of the detent mechanism of the present invention;

FIG. 8 is a perspective view of a clamp mechanism drive collar of the present clamp coagulator apparatus;

DETAILED DESCRIPTION

Figure 3:
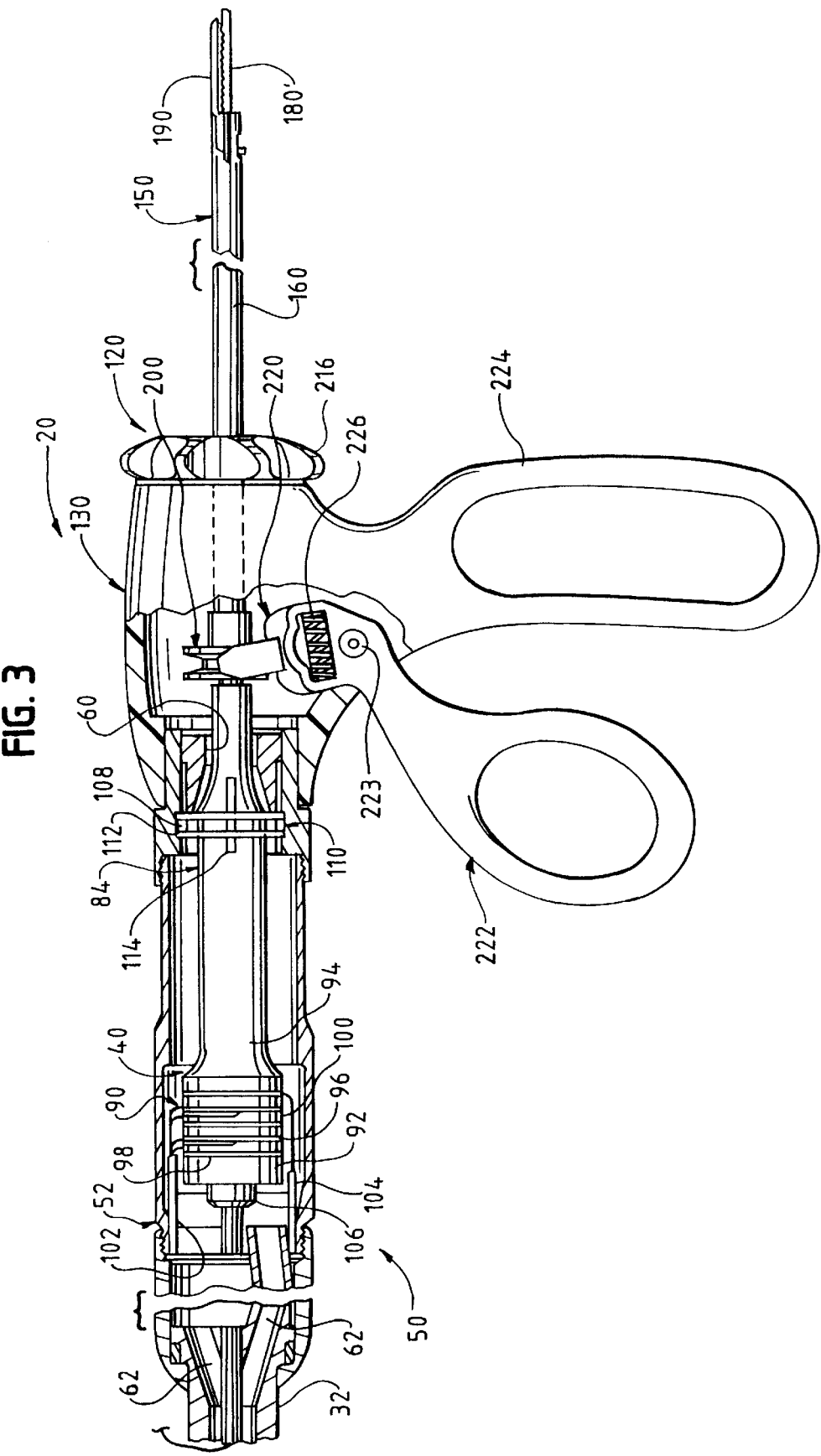
FIG. 3 is a side elevational view, partially in cut-away, of the clamp coagulator embodying the principles of the present invention, shown in operative association with an ultrasonic drive unit of the surgical system shown in FIG. 1.

While the present invention is susceptible of embodiments in various forms, there is shown in the drawings and will hereinafter be described a presently preferred embodiment, with the understanding that the present disclosure is to be considered as an exemplification of the invention, and is not intended to limit the invention to the specific embodiment illustrated.

The present invention is particularly directed to an improved ultrasonic surgical clamp coagulator apparatus which is configured for effecting tissue coagulation, and/or clamping during surgical procedures. The present apparatus can readily be configured for use in both open surgical procedures, as well as laparoscopic or endoscopic procedures. Versatile use is facilitated by selective use of ultrasonic energy. When ultrasonic components of the apparatus are inactive, tissue can be readily gripped and manipulated, as desired, without tissue cutting or damage. When the ultrasonic components are activated, the apparatus permits tissue to be gripped for coupling with the ultrasonic energy to effect tissue coagulation, with application of increased pressure efficiently effecting tissue cutting and coagulation. If desired, ultrasonic energy can be applied to tissue without use of the clamping mechanism of the apparatus by appropriate manipulation of the ultrasonic "blade" or end-effector of the device.

As will become apparent from the following description, the present clamp coagulator apparatus is particularly configured for disposable use by virtue of its straightforward construction. As such, it is contemplated that the apparatus be used in association with an ultrasonic drive unit of a surgical system, whereby ultrasonic energy from the drive unit provides the desired ultrasonic actuation of the present clamp coagulator apparatus. It will be appreciated that a clamp coagulator apparatus embodying the principles of the present invention can be configured for non-disposable use, and non-detachably integrated with an associated ultrasonic drive unit. However, detachable connection of the present clamp coagulator apparatus with an associated ultrasonic drive unit is presently preferred for single-patient use of the apparatus.

With reference first to FIGS. 1 and 3, therein is illustrated a presently preferred embodiment of a surgical system, generally designated 10, which includes an ultrasonic clamp coagulator apparatus embodying the principles of the present invention. Preferred details of the ultrasonic generator and associated ultrasonic drive unit of the surgical system 10 will first be described, with subsequent detailed description of the ultrasonic surgical clamp coagulator apparatus, including a clamp mechanism configured for indexed rotation, embodying the principles of the present invention.

The surgical system 10 includes an ultrasonic generator 30 and an associated ultrasonic surgical instrument. The surgical instrument includes an ultrasonic drive unit, designated 50, and an ultrasonic clamp coagulator apparatus 120 embodying the principles of the present invention. As will be further described, an ultrasonic transducer of the drive unit 50, and an ultrasonic waveguide of the clamp coagulator 120, together provide an acoustic assembly of the present surgical system, with the acoustic assembly providing ultrasonic energy for surgical procedures when powered by generator 30. It will be noted that in some applications, the ultrasonic drive unit 50 is referred to as a "hand piece assembly" because the surgical instrument of the surgical system is configured such that a surgeon grasps and manipulates the ultrasonic drive unit 50 during various procedures and operations. The clamp coagulator apparatus 120 embodying the principles of the present invention preferably includes a scissors-like grip arrangement which facilitates positioning and manipulation of the instrument apart from manipulation of the ultrasonic drive unit 50.

The generator 30 of the surgical system sends an electrical signal through a cable 32 at a selected excursion, frequency, and phase determined by a control system of the generator 30. As will be further described, the signal causes one or more piezoelectric elements of the acoustic assembly of the surgical instrument to expand and contract, thereby converting the electrical energy into mechanical motion. The mechanical motion results in longitudinal waves of ultrasonic energy that propagate through the acoustic assembly in an acoustic standing wave to vibrate the acoustic assembly at a selected frequency and excursion. An end-effector at the distal end of the waveguide of the acoustic assembly is placed in contact with tissue of the patient to transfer the ultrasonic energy to the tissue. As further described below, a surgical tool, such as, a jaw or clamping mechanism, is preferably utilized to press the tissue against the end-effector.

As the end-effector couples with the tissue, thermal energy or heat is generated as a result of friction, acoustic absorption, and viscous losses within the tissue. The heat is sufficient to break protein hydrogen bonds, causing the highly structured protein (i.e., collagen and muscle protein) to denature (i.e., become less organized). As the proteins are denatured, a sticky coagulum forms to seal or coagulate small blood vessels. Deep coagulation of larger blood vessels results when the effect is prolonged.

The transfer of the ultrasonic energy to the tissue causes other effects including mechanical tearing, cutting, cavitation, cell disruption, and emulsification. The amount of cutting as well as the degree of coagulation obtained varies with the excursion of the end-effector, the frequency of vibration, the amount of pressure applied by the user, the sharpness of the end-effector, and the coupling between the end-effector and the tissue.

As illustrated in FIG. 1, the generator 30 includes a control system integral with the generator 30, a power switch 34, and a triggering mechanism 36. The power switch 34 controls the electrical power to the generator 30, and when activated by the triggering mechanism 36, the generator 30 provides energy to drive the acoustic assembly of the surgical system 10 at a predetermined frequency and to drive the end-effector at a predetermined excursion level. The generator 30 drives or excites the acoustic assembly at any suitable resonant frequency of the acoustic assembly.

When the generator 30 is activated via the triggering mechanism 36, electrical energy is continuously applied by the generator 30 to a transducer stack or assembly 40 of the acoustic assembly. A phase-locked loop in the control system of the generator 30 monitors feedback from the acoustic assembly. The phase lock loop adjusts the frequency of the electrical energy sent by the generator 30 to match the resonant frequency of the selected longitudinal mode of vibration of the acoustic assembly including the tissue load. In addition, a second feedback loop in the control system maintains the electrical current supplied to the acoustic assembly at a preselected constant level in order to achieve substantially constant excursion at the end-effector of the acoustic assembly.

The electrical signal supplied to the acoustic assembly will cause the distal end of the waveguide, i.e., the end-effector, to vibrate longitudinally in the range of, for example, approximately 20 kHz to 250 kHz, and preferably in the range of about 54 kHz to 56 kHz, and most preferably at about 55.5 kHz. The excursion of the vibrations at the end-effector can be controlled by, for example, controlling the amplitude of the electrical signal applied to the transducer assembly 40 of the acoustic assembly by the generator 30.

As noted above, the triggering mechanism 36 of the generator 30 allows a user to activate the generator 30 so that electrical energy may be continuously supplied to the acoustic assembly. The triggering mechanism 36 preferably comprises a foot activating switch that is detachably coupled or attached to the generator 30 by a cable or cord. Alternatively, the triggering mechanism can be configured as a hand switch incorporated in the ultrasonic drive unit 50 to allow the generator 30 to be activated by a user.

The generator 30 also has a power line 38 for insertion in an electro-surgical unit or conventional electrical outlet. It is contemplated that the generator 30 can also be powered by a direct current (DC) source, such as a battery. The generator 30 can comprise any suitable generator, such as Model No. GEN01, available from Ethicon Endo-Surgery, Inc.

Referring to FIGS. 1 and 3, the ultrasonic drive unit 50 of the surgical instrument includes a multi-piece housing 52 adapted to isolate the operator from the vibrations of the acoustic assembly. The drive unit housing 52 can be shaped to be held by a user in a conventional manner, but it is contemplated that the present clamp coagulator 120 principally be grasped and manipulated by a scissors-like arrangement provided by a housing of the apparatus, as will be described. While the multi-piece housing 52 is illustrated, the housing 52 may comprise a single or unitary component.

The housing 52 of the ultrasonic drive unit 50 generally includes a proximal end, a distal end, and a cavity extending longitudinally therein. The distal end of the housing 52 includes an opening 60 configured to allow the acoustic assembly of the surgical system 10 to extend therethrough, and the proximal end of the housing 52 is coupled to the generator 30 by the cable 32. The cable 32 preferably includes ducts or vents 62 to allow air to be introduced into the housing 52 of the ultrasonic drive unit 50 to cool the transducer assembly 40 of the acoustic assembly.

The housing 52 of the ultrasonic drive unit 50 is preferably constructed from a durable plastic, such as Ultem®. It is also contemplated that the housing 52 may alternatively be made from a variety of materials including other plastics [i.e. liquid crystal polymer (LCP), nylon, or polycarbonate]. A suitable ultrasonic drive unit 50 is Model No. HP050, available from Ethicon Endo-Surgery, Inc.

The acoustic assembly of the surgical instrument generally includes a first acoustic portion and a second acoustic portion. The first acoustic portion is preferably carried by the ultrasonic drive unit 50, and the second acoustic portion (in the form of a waveguide and end-effector, as will be described) is carried by the ultrasonic clamp coagulator apparatus. The distal end of the first acoustic portion is operatively coupled to the proximal end of the second acoustic portion preferably by a threaded connection.

As shown in FIG. 3, the first acoustic portion includes the transducer stack or assembly 40 and a mounting device 84, and the second acoustic portion includes a transmission component or working member, referred to herein as a waveguide having an end-effector.

The components of the acoustic assembly are preferably acoustically tuned such that the length of each component is an integral number of one-half wavelengths ($n\lambda/2$), where the wavelength $\lambda$ is the wavelength of a preselected or operating longitudinal vibration frequency $f_0$ of the acoustic assembly, and n is any non-negative integer. It is also contemplated that the acoustic assembly may incorporate any suitable arrangement of acoustic elements.

The transducer assembly 40 of the acoustic assembly converts the electrical signal from the generator 30 into mechanical energy that results in longitudinal vibratory motion of the end-effector at ultrasonic frequencies. When the acoustic assembly is energized, a vibratory motion standing wave is generated through the acoustic assembly.

The excursion of the vibratory motion at any point along the acoustic assembly depends on the location along the acoustic assembly at which the vibratory motion is measured. A minimum or zero crossing in the vibratory motion standing wave is generally referred to as a node (i.e., where motion is usually minimal), and an absolute value maximum or peak in the standing wave is generally referred to as an anti-node. The distance between an anti-node and its nearest node is one-quarter wavelength ($\lambda/4$).

As shown in FIG. 3, the transducer assembly 40 of the acoustic assembly, which is also known as a "Langevin stacks", generally includes a transduction portion 90, a first resonator 92, and a second resonator 94. The transducer assembly is preferably an integral number of one-half system wavelengths ($n\mu/2$) in length. It is to be understood that the present invention may be alternatively configured to include a transducer assembly comprising a magnetostrictive, electromagnetic or electrostatic transducer.

The distal end of the first resonator 92 is connected to the proximal end of transduction section 90, and the proximal end of the second resonator 94 is connected to the distal end of transduction portion 90. The first and second resonators 92 and 94 are preferably fabricated from titanium, aluminum, steel, or any other suitable material, and most preferably, the first resonator 92 is fabricated from 303 stainless steel and the second resonator 94 is fabricated from 7075-T651 Aluminum. The first and second resonators 92 and 94 have a length determined by a number of variables, including the length of the transduction section 90, the speed of sound of material used in the resonators 92 and 94, and the desired fundamental frequency $f_0$ of the transducer assembly 40. The second resonator 94 can be tapered inwardly from its proximal end to its distal end to function as a velocity transformer and amplify the ultrasonic vibration excursion.

The transduction portion 90 of the transducer assembly 40 preferably comprises a piezoelectric section of alternating positive electrodes 96 and negative electrodes 98, with piezoelectric elements 100 alternating between the electrodes 96 and 98. The piezoelectric elements 100 can be fabricated from any suitable material, such as, for example, lead zirconate-titanate, lead metaniobate, lead titanate, or other piezoelectric material. Each of the positive electrodes 96, negative electrodes 98, and piezoelectric elements 100 have a bore extending through the center. The positive and negative electrodes 96 and 98 are electrically coupled to wires 102 and 104, respectfully. The wires 102 and 104 transmit the electrical signal from the generator 30 to electrodes 96 and 98.

As illustrated in FIG. 3, the piezoelectric elements 100 are held in compression between the first and second resonators 92 and 94 by a bolt 106. The bolt 106 preferably has a head, a shank, and a threaded distal end. The bolt 106 is inserted from the proximal end of the first resonator 92 through the bores of the first resonator 92, the electrodes 96 and 98, and piezoelectric elements 100. The threaded distal end of the bolt 106 is screwed into a threaded bore in the proximal end of second resonator 94. The bolt can be fabricated from steel, titanium, aluminum, or other suitable material and is preferably fabricated from Ti-6Al-4V Titanium, and most preferably from 4037 low alloy steel.

The piezoelectric elements 100 are energized in response to the electrical signal supplied from the generator 30 to produce an acoustic standing wave in the acoustic assembly. The electrical signal causes an electro-magnetic field across the piezoelectric elements 100, causing the piezoelectric elements 100 to expand and contract in a continuous manner along the axis of the voltage gradient, producing high frequency longitudinal waves of ultrasonic energy. The ultrasonic energy is transmitted through the acoustic assembly to the end-effector.

The mounting device 84 of the acoustic assembly has a proximal end, a distal end, and preferably has a length substantially equal to an integral number one-half system wavelengths. The proximal end of the mounting device 84 is preferably axially aligned and coupled to the distal end of the second resonator 94 by an internal Treaded connection near an anti-node. (For purposes of this disclosure, the term "near" is defined as "exactly at" or "in close proximity to".) It is also contemplated that the mounting device 84 may be attached to the second resonator 94 by any suitable means, and the second resonator 94 and mounting device 84 may be formed as a single or unitary component.

The mounting device 84 is coupled to the housing 52 of the ultrasonic drive unit 50 near a node. The mounting device 84 preferably includes an integral mounting flange 108 disposed around its periphery. The mounting flange 108 is preferably disposed in an annular groove 110 formed in the housing 52 of the ultrasonic drive unit 50 to couple the mounting device 84 to the housing 52. A compliant member or material 112, such as a pair of silicone rubber O-rings attached by stand-offs, may be placed between the annular groove 110 of the housing 52 and the integral flange 108 of the mounting device 86 to reduce or prevent ultrasonic vibration from being transmitted from the mounting device 84 to the housing 52.

The mounting device 84 is preferably secured in a pre-determined axial position by a plurality of pins 114, preferably four. The pins 114 are disposed in a longitudinal direction ninety (90) degrees apart from each other around the outer periphery of the mounting device 84. The pins 114 are coupled to the housing 52 of the ultrasonic drive unit 50 and are disposed through notches in the acoustic mounting flange 108 of the mounting device 84. The pins 114 are preferably fabricated from stainless steel.

The mounting device 84 is preferably configured to amplify the ultrasonic vibration excursion that is transmitted through the acoustic assembly to the distal end of the end-effector. In one preferred embodiment, the mounting device 84 comprises a solid, tapered horn. As ultrasonic energy is transmitted through the mounting device 84, the velocity of the acoustic wave transmitted through the mounting device 84 is amplified. It is contemplated that the mounting device 84 be configured as any suitable shape, such as, for example, a stepped horn, a conical horn, an exponential horn, a unitary gain horn, or the like.

As shown in FIG. 3, the mounting device 84 is preferably acoustically coupled to the second acoustic portion of the ultrasonic clamp coagulator apparatus 120. The distal end of the mounting device 84 is preferably coupled to the proximal end of the second acoustic portion by an internal threaded connection near an anti-node, but alternative coupling arrangements can be employed.

Figure 4:
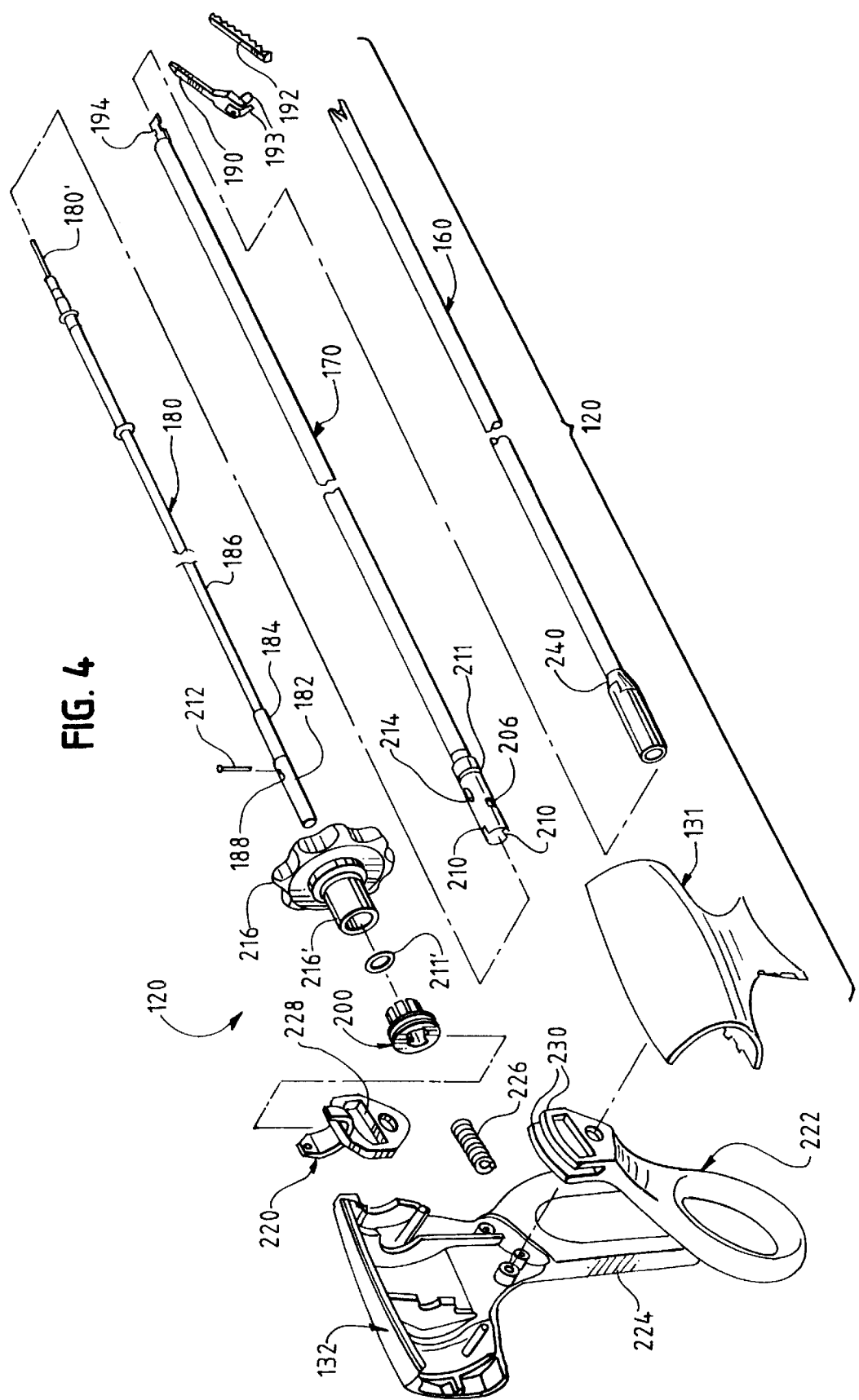
FIG. 4 is an exploded view of the ultrasonic surgical clamp coagulator apparatus embodying the principles of the present invention.

Referring now to FIG. 4, an exploded view of the ultrasonic clamp coagulator apparatus 120 of the surgical system 10 in accordance with a preferred embodiment is illustrated. The proximal end of the ultrasonic clamp coagulator apparatus 120 preferably receives and is fitted to the distal end of the ultrasonic drive unit 50 by insertion of the drive unit into the housing of the apparatus, as shown in FIG. 3. The ultrasonic clamp coagulator apparatus 120 is preferably attached to and removed from the ultrasonic drive unit 50 as a unit. The ultrasonic clamp coagulator 120 may be disposed of after a single use.

The ultrasonic clamp coagulator apparatus 120 preferably includes a handle assembly or a housing 130, preferably comprising mating housing portions 131, 132, and an elongated or endoscopic portion 150. When the present apparatus is configured for endoscopic use, the construction can be dimensioned such that portion 150 has an outside diameter of about 5.5 Mm. The elongated portion 150 of the ultrasonic clamp coagulator apparatus 120 extends orthogonally from the apparatus housing 130. The elongated portion 150 can be selectively rotated with respect to the housing 130 as further described below. The elongated portion 150 preferably includes an outer tubular member or sheath 160, an inner tubular actuating member 170, and the second acoustic portion of the acoustic system in the form of a waveguide 180 having an end-effector 180'. As will be described, the outer sheath 160, the actuating member 170, and the waveguide 180 are preferably joined together for indexed rotation as a unit (together with ultrasonic drive unit 50) relative to housing 130.

As illustrated in FIG. 4, the proximal end of the waveguide 180 of the second acoustic portion is preferably detachably coupled to the mounting device 84 of the ultrasonic drive unit 50 near an anti-node as described above.

The waveguide 180 preferably has a length substantially equal to an integer number of one-half system wavelengths ($n\lambda/2$). The waveguide 180 is preferably fabricated from a solid core shaft constructed out of material which propagates ultrasonic energy efficiently, such as titanium alloy (i.e., Ti-6Al-4V) or an aluminum alloy. It is contemplated that the waveguide 180 can alternatively be fabricated from any other suitable material.

The waveguide is preferably substantially semi-flexible. It will be recognized that the waveguide can alternatively be substantially rigid or may comprise a flexible wire. The waveguide may be configured to amplify the is mechanical vibrations transmitted through the waveguide to the end-effector as is well known in the art. The waveguide may further have features to control the gain of the longitudinal vibration along the waveguide and features to tune the waveguide to the resonant frequency of the system.

It will be recognized that the waveguide 180 may have any suitable cross-sectional dimension. For example, the waveguide may have a substantially uniform cross-section or the waveguide may be tapered at various sections or may be tapered along its entire length.

As shown in FIG. 4, the waveguide 180 generally has a first section 182, a second section 184, and a third section 186. The first section 182 of the waveguide extends distally from the proximal end of the waveguide, and has a substantially continuous cross-section dimension.

The first section 182 preferably includes at least one radial hole or aperture 188 extending diametrically therethrough, substantially perpendicular to the axis of the waveguide 180. The aperture 188 is preferably positioned at a node, but may be otherwise positioned. It will be recognized that the aperture 188 may have any suitable depth and may be any suitable shape. The aperture is configured to receive a connector pin member which connects the waveguide 180, the tubular actuating member 170, and the tubular outer sheath 160 together for conjoint, indexed rotation relative to apparatus housing 130.

The second section 184 of the waveguide 180 extends distally from the first section 182. The second section 184 preferably also has a substantially continuous cross-section. The diameter of the second section 184 is smaller than the diameter of the first section 182 and larger than the diameter of the third section 186. As ultrasonic energy passes from the first section 182 of the waveguide 180 into the second section 184, the narrowing of the second section 184 will result in an increased amplitude of the ultrasonic energy passing therethrough.

The third section 186 extends distally from the distal end of the second section 184. The third section 186 also has a substantially continuous cross-section. The third section 186 may also include small diameter changes along its length. As ultrasonic energy passes from the second section 184 of the waveguide 180 into the third section 186, the narrowing of the third section 186 will result in an increased amplitude of the ultrasonic energy passing therethrough.

The third section 186 may have a plurality of grooves or notches (not shown) formed in its outer circumference. The grooves may be located at nodes of the waveguide 180 to act as alignment indicators for the installation of a damping sheath (not shown) and stabilizing silicone rings or compliant supports during manufacturing. Such compliant supports desirably act to isolate the active waveguide 180 form surrounding components of the apparatus. A seal is preferably provided at the distal-most node, nearest the end-effector 180', to abate passage of tissue, blood, and other material in the region between the waveguide and actuating member 170. As her described hereinafrer, and in accordance with the present invention, a support member is preferably provided at the distal-most node to resist bending moments created in the waveguide by the associated clamping mechanism, and to effect sealing of the region between the waveguide and actuating member 170. Even though it is contemplated that the support member be relatively thin (with regions as thin as about 0.003 to 0.005 inches) to provide the desired support, acoustic isolation of the active waveguide from actuating member 170 is effected.

The end-effector 180' of the waveguide 180 is preferably integral therewith and formed as a single unit. The end-effector may alternately be connected by a threaded connection, or by a welded joint. The distal end of the end-effector is disposed near an anti-node in order to tune the acoustic assembly to a preferred resonant frequency $f_o$ when the acoustic assembly is not loaded by tissue. When the transducer assembly is energized, the distal end of the end-effector is configured to move longitudinally in the range of, for example, approximately 10–500 microns peak-to-peak, and preferably in the range of about 10 to about 100 microns at a predetermined vibrational frequency $f_o$.

In accordance with the illustrated embodiment, the end-effector 180', sometimes referred to as a blade, is preferably cylindrical for cooperation with the associated clamping mechanism of the present clamp coagulator apparatus. The end-effector may receive suitable surface treatment, as is known in the art.

With particular reference to FIG. 2, therein is illustrated the clamping mechanism of the present clamp coagulator 120, which is configured for cooperative action with the end-effector 180' of the waveguide 180. The clamping mechanism includes a pivotally movable clamp arm 190, which is pivotally connected at the distal end thereof to the distal end of outer tubular sheath 160. A clamp pad 192, preferably formed from Teflon or other suitable low-friction material, is mounted on the surface of the clamp arm for cooperation with the end-effector 180', with pivotal movement of the clamp arm positioning the clamp pad in substantially parallel relationship to, and in contact with, the end-effector 180'. By this construction, tissue to be clamped is grasped between the pad 192 and the end effector 180'. As illustrated, the pad 192 is preferably provided with a sawtooth-like configuration to enhance the gripping of tissue in cooperation with the end-effector 180'.

Pivotal movement of the clamp arm with respect to the end-effector is effected by the provision of at least one, and preferably a pair of lever portions 193 of the clamp arm 190 at the proximal end thereof. The lever portions are positioned on respective opposite sides of the waveguide 180 and end-effector 180', and are in operative engagement with a drive portion 194 of the reciprocable actuating member 170. Reciprocable movement of the actuating member, relative to the outer tubular sheath 160 and the waveguide 180, thereby effects pivotal movement of the clamp arm relative to the end-effector. The lever portions 193 can be respectively positioned in a pair of openings defined by the drive portion 194, or otherwise suitably mechanically coupled therewith, whereby reciprocable movement of the actuating member acts through the drive portion 194 and lever portions 193 to pivot the clamp arm.

Figure 5:
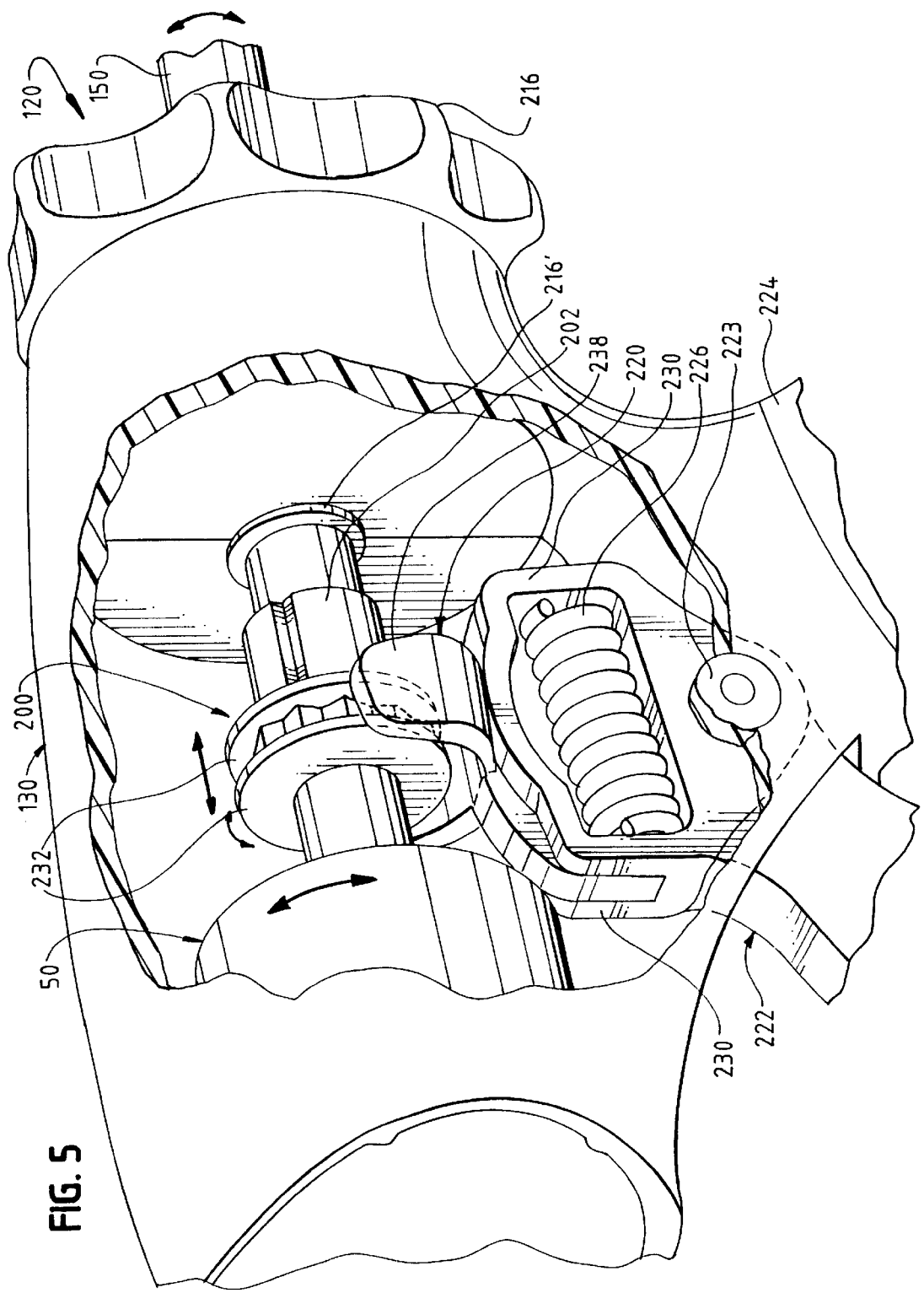
FIG. 5 is an enlarged, fragmentary view of the present clamp coagulator apparatus illustrating a clamp drive mechanism thereof and associated detent mechanism.
Figure 6:
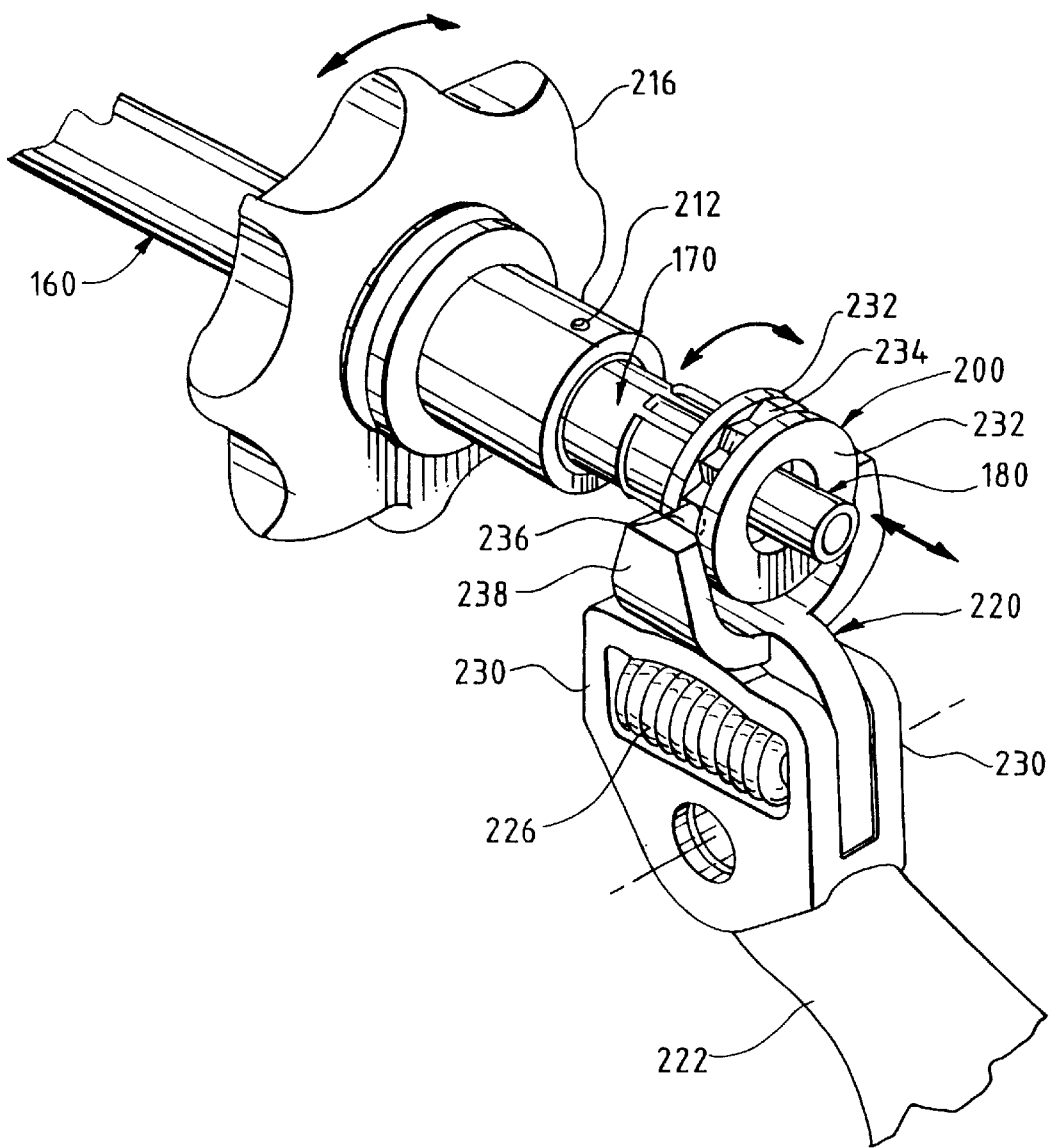
FIG. 6 is a diagrammatic view further illustrating the clamp drive mechanism and detent mechanism of the present clamp coagulator apparatus.

With particular reference to FIGS. 3, 5, and 6, reciprocable movement of the actuating member 170 is effected by the provision of a drive collar, generally designated 200, mounted on the proximal end of the actuating member for conjoint rotation. To this end, the drive collar includes a pair of diametrically opposed axially extending arms 202 each having a drive lug 204, with the drive lugs being biased by the arms 202 into engagement with suitable openings 206 defined by the proximal portion of tubular actuating member 170. Rotation of the drive collar 200 together with the actuating member 170 is further effected by the provision of a pair of keys 208 (see FIG. 8) diametrically engageable with suitable openings 210 defined by the proximal end of the actuating member 170. A circumferential groove 211 on the actuating member 170 receives on O-ring 211' (FIG. 4) for engagement with the inside surface of outer sheath 160.

Rotation of the actuating member 170 together with tubular outer sheath 160 and inner waveguide 180 is provided by a connector pin 212 extending through these components of the apparatus. As illustrated in FIG. 4, the tubular actuating member 170 defines an elongated slot 214 through which the connector pin 212 extends to accommodate reciprocable movement of the actuating member relative to the outer tubular sheath and inner waveguide.

A rotation knob 216 mounted on the outer tubular sheath facilitates rotational positioning of the elongated portion 150 with respect to the housing 130 of the clamp coagulator apparatus. Connector pin 212 preferably joins knob 216 together with sheath 160, member 170, and waveguide 180 for rotation as a unit relative to housing 130. In a current embodiment, hub portion 216' of the rotation knob acts to rotatably mount the outer sheath 160, the actuating member 170, and the waveguide 180 (as a unit with knob 216), on the housing 130.

The drive collar 200 provides a portion of the clamp drive mechanism of the apparatus which effects pivotal movement of the clamp arm 190 by reciprocation of actuating member 170. The clamp drive mechanism further includes a drive yoke 220 which is operatively connected with an operating lever 222 of the apparatus, with the operating lever thus interconnected with the reciprocable actuating member 170 via drive yoke 220 and drive collar 200. The operating lever 222 is pivotally connected to the housing 130 of the apparatus (by a pivot mount 223) for cooperation in a scissors-like fashion with a handgrip portion 224 of the housing. Movement of lever 222 toward handgrip portion 224 translates actuating member 170 proximally, thereby pivoting clamp arm 190 toward end-effector 180'.

Operative connection of the drive yoke 220 with the operating lever 222 is provided by a spring 226, preferably comprising a compression coil spring. The spring 226 fits within a spring slot 228 defined by the drive yoke 220, which in turn is positioned between a pair of spring retainer flanges 230 of the operating lever 222. The drive yoke 220 is pivotally movable with respect to the spring flanges 230 (about pivot mount 223 of housing 130) in opposition to the compression coil spring, which bears against the surfaces of the spring slots defined by each of the spring flanges 230. In this manner, the force which can be applied to the actuating member 170, by pivotal movement of operating lever 222 acting through drive yoke 220 and drive collar 200, is limited by the force with which spring 226 bears against the spring flanges 230. Application of excessive force results in pivotal displacement of drive yoke 220 relative to the spring flanges 230 of the operating lever 222 in opposition to spring 226. In a presently preferred embodiment, spring 226 is selected to limit clamping force at clamp arm 190 to approximately 2 pounds. Stop portions of housing 130 limit the travel of operating lever 222 to prevent excessive compression of spring 226.

Indexed rotational positioning of the elongated portion 150 of the present clamp coagulator apparatus 120 is provided by the provision of a detent mechanism incorporated into the clamp drive mechanism of the apparatus. Specifically, the drive collar 200 includes a pair of axially spaced apart drive flanges 232. A detent-receiving surface is provided between the drive flanges 232, and defines a plurality of circumferentially spaced teeth 234 which define detent-receiving depressions generally about the periphery of the drive collar 200. In a presently preferred embodiment, twelve (12) of the teeth 234 are provided, thereby providing indexed positioning of the elongated portion 150 of the apparatus at 30° intervals relative to the housing 130 of the apparatus.

Indexed rotational movement is further achieved by the provision of at least one, and preferably a pair, of diametrically opposed detents 236 respectively provided on cantilevered yoke arms 238 of drive yoke 220. By this arrangement, the yoke arms 238 are positioned between the drive flanges 232 for engagement with the confronting surfaces thereof and bias the detents 236 into engagement with the drive collar 200. Indexed relative rotation is thus achieved, with the detents 236 of the yoke arms cooperating with the drive flanges 238 for effecting reciprocation of the actuating member 170. In a presently preferred embodiment, the drive yoke 220 is formed from suitable polymeric material, with the biasing force created by the yoke arms acting on the detents thereof cooperating with the radial depressions defied by the drive collar to resist relative rotational torque less than about 5 to 20 inch-ounces. As such, the elongated portion 150 of the clamp coagulator apparatus is maintained in any of its selected indexed rotational positions, relative to housing 130, unless a torque is applied (such as by rotation knob 216) exceeding this predetermined torque level. A snap-like indexing action is thus provided.

Rotation of the elongated proportion 150 of the present clamp coagulator apparatus 120 is preferably effected together with relative rotational movement of ultrasonic drive unit 50 with respect to apparatus housing 130. In order to join the elongated portion 150 to the ultrasonic drive unit 50 in ultrasonic-transmitting relationship, the proximal portion of the outer tubular sheath 160 is preferably provided with a pair of wrench flats 240 (see FIG. 4). The wrench flats allow torque to be applied by a suitable torque wrench or the like to thereby permit the waveguide 180 to be joined to the ultrasonic drive unit 50. The ultrasonic drive unit, as well as the elongated portion 150, are thus rotatable, as a unit, by suitable manipulation of rotation knob 216, relative to housing 130 of the apparatus. The interior of housing 130 is dimensioned to accommodate such relative rotation of the drive unit 50.

Figure 9:
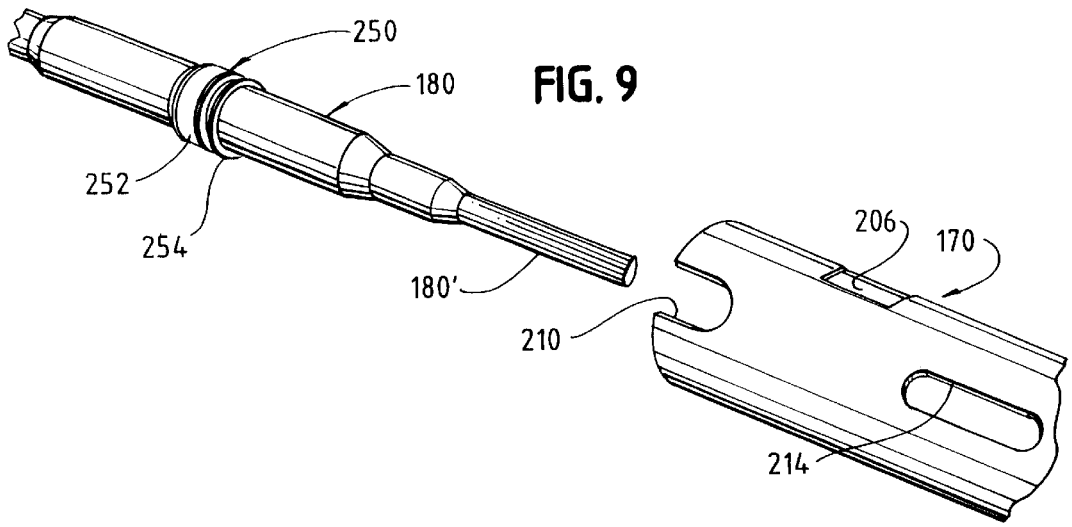
FIG. 9 is a fragmentary, exploded perspective view illustrating a waveguide of the present apparatus, having a support member positioned thereon embodying the principles of the present invention, illustrated with an associated reciprocable actuating member of the apparatus.

As noted above, the present surgical clamp coagulator apparatus preferably includes a support member positioned at the distal-most node of the waveguide 180 to resist bending moments created in the waveguide by pivotal movement of clamp arm 190 against end-effector 180'. A support member, designated 250 in FIGS. 9–15, and embodying the principles of the present invention, is particularly preferred by virtue of the combination of support and sealing functions provided by the support member. The support member has been particularly configured to permit the waveguide 180 to be provided with a relatively large cross-sectional area, even though the outer tubular sheath 160 of elongated portion 150 of the present surgical apparatus is preferably provided with an outside diameter less than about 6 mm. The support member desirably acts to acoustically isolate the active waveguide 180 from the surrounding actuating member 170, while providing support to resist bending moments created in the waveguide, as well as effecting sealing between the waveguide and the relatively reciprocable actuating member. illustrated in FIG. 9 and 10, the annular support member 250 includes an annular support portion 252 having a generally cylindrical outer support surface which is positioned for engagement with the interior of reciprocable support member 170. The support member 250 is preferably formed from elastomeric material, such a silicone rubber, thus providing the desired compliance for the sealing function of the support member. However, it is contemplated that the support portion 252 be formed sufficiently thin to minimize its compression to aid in resisting bending moments created in the waveguide, particularly at the distal-most node thereof, as clamp arm 190 presses tissue against end-effector 180'. It is contemplated that the thickness of the support portion, at its thinnest region, be on the order of 0.003–0.005 inches, and formed from material exhibiting a durometer on the order of 60 Shore A. Even when configured to include such relatively thin regions, the support member still provides desired acoustic isolation for the waveguide.

As illustrated, the support member 250 further includes an integral annular sealing portion 254. In the embodiments of the support member 250 illustrated in FIGS 10 and 11, the sealing portion 254 is spaced axially distally from the support portion 252. As shown, the sealing portion 254 preferably includes a pair of converging surfaces (each preferably generally frusto-conical), which converge and meet each other to define a thin and compliant peripheral sealing region of the sealing portion 254. In a non-compressed state, this sealing region is spaced radially outwardly of the support surface of the support portion 252. This preferred configuration of the sealing member accommodates reciprocation of tubular actuating member 170 with respect to the waveguide 180, while desirably sealing the region between the waveguide and the actuating member against fluids and other material encountered in surgery. It is preferred that an annular recess 255 be provided intermediate support portion 252 and sealing portion 154 (in those embodiments in which the sealing portion is spaced axially of the support portion) to accommodate deflection of the sealing portion toward the support portion attendant to relative reciprocation of the actuating member 170.

As shown, the sealing member 250 is preferably positioned with respect to the distal-most node, designated "N" in the illustrations, such that the support portion 252 is generally centered with respect to the node. As will be observed, the embodiment of FIG. 11 differs from the embodiment of FIG. 10, in that the waveguide 180 is provided with a lug portion 181 having an outside diameter which is greater than the portions of the waveguide adjacent to the lug portion. In this embodiment of support member 250, the support portion 252 is preferably centered at the node "N", and is positioned on and flanks the lug portion of the waveguide. The lug portion acts to maintain the support member in position of the waveguide attendant to relative reciprocation of actuating member 170.

Figure 10:
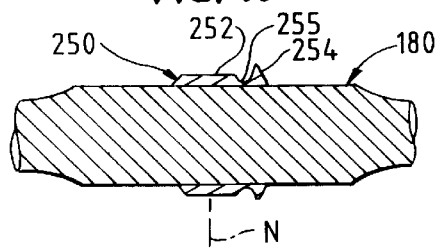
FIG. 10–15 are fragmentary cross-sectional views of the waveguide illustrated in FIG. 9, with various embodiments of the support member of the present invention illustrated in position on the waveguide.
Figure 11:
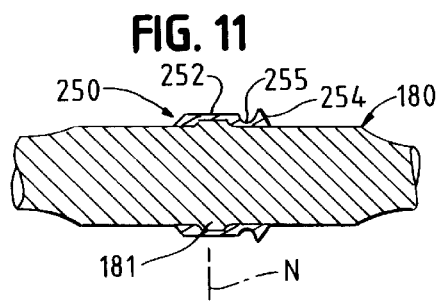
Figure 12:
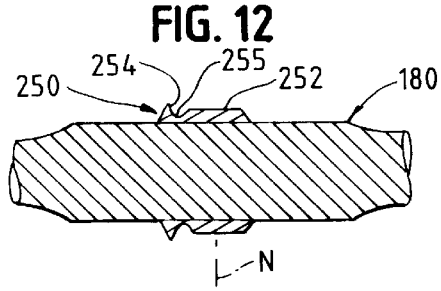
Figure 13:
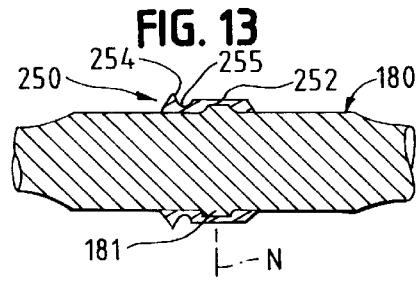

Referring now to the embodiments of FIGS. 12 and 13, the embodiments of the support member 250 illustrated therein are generally similar to the embodiments illustrated in FIGS. 10 and 11, respectively. However, the embodiments of FIGS. 12 and 13 differ in that the sealing portion 254 of each illustrated support member 250 is spaced axially proximally of the corresponding support portion 252. Again, in the embodiment illustrated in FIG. 13 wherein waveguide 180 includes a lug portion 181, the support portion 252 is preferably positioned an and flanks the lug portion.

Figure 14:
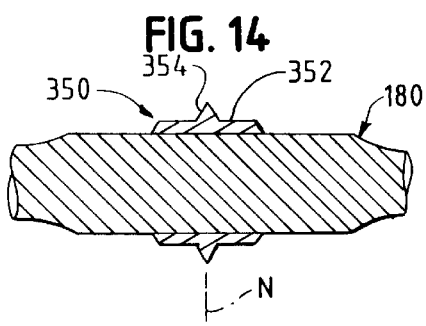
Figure 15:
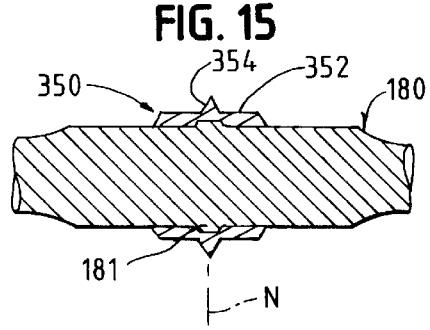

Referring now to FIGS. 14 and 15, further alternate embodiments of the present support member, designated 350, are illustrated. Each of these embodiments also include a support portion, designated 352, having a generally cylindrical outer support surface. These embodiments further include a sealing portion, designated 354, having a pair of converging surfaces which converge and meet to define a peripheral sealing region spaced radially outwardly of the outer support surface. In distinction from previous embodiments, these embodiments include a sealing portion 354 which is positioned medially of the support portion 352. In the embodiment of FIG. 15, wherein waveguide includes a lug portion 181, the sealing portion 354 is positioned in substantial alignment with the lug portion of the waveguide.

A support member embodying the principles of the present invention desirably isolates the ultrasonic vibration transmitted through waveguide 180 from the surrounding sheath, in particular, tubular actuating member 170.

Disposition of the present support member at the distal-most node of the waveguide desirably resists bending moments created in the waveguide as the clamping mechanism of the apparatus is operated. Disposition at the distal-most node of the waveguide also effects sealing of the region between the waveguide and the actuating member. While formation of the present support member from silicone rubber is presently preferred, it will be understood that other materials may alternatively be employed.

Thus, the present surgical clamp coagulator apparatus is configured for highly efficient and versatile use, with the construction being sufficiently straight-forward and economical in configuration to permit single-patient use.

Components of the apparatus can be fabricated from materials suited for surgical applications. By virtue of the detent mechanism provided by cooperation of drive collar 200 and drive yoke 220, selective angular positioning of the elongated portion 150 of the apparatus, and the associated ultrasonic drive unit 50, is readily effected with respect to the housing 130 of the apparatus. The scissors-like action provided by pivotal operating lever 222 and cooperating handgrip portion 224 facilitates convenient and efficient manipulation and positioning of the apparatus, and operation of the clamping mechanism at the distal portion of the apparatus whereby tissue is efficiently urged against the end-effector 180'. The detent mechanism resists rotation of the ultrasonic drive unit, and associated cable assembly, with respect to the housing 130 with the resistence to rotation readily and conveniently overcome by application of sufficient torque via rotation knob 216. The preferred provision of a combination support and sealing member at the distal-most node of the apparatus further facilitate efficient operation and configuration of the instrument with a selectively small cross-section.

From the foregoing, it will be observed that numerous modifications and variations can be effected without departing from the true spirit and scope of the novel concept of the present invention. It is to be understood that no limitation with respect to the specific embodiment illustrated herein is intended or should be inferred. The disclosure is intended to cover, by the appended claims, all such modifications as fall within the scope of the claims.

What is claimed is:

1. An ultrasonic surgical clamp apparatus comprising:
   a housing;
   an outer tubular sheath having a proximal end joined to said housing, and a distal end;
   an inner actuating member reciprocably positioned within said outer tubular sheath;
   an ultrasonic waveguide positioned within said inner tubular actuating member and having an end-effector extending distally of said distal end of said outer tubular sheath, said actuating member being reciprocable relative to said waveguide;
   a clamp arm pivotally mounted on said distal end of said outer tubular sheath for pivotal movement with respect to said end-effector for clamping tissue between said clamp arm and said end-effector, said clamp arm being operatively connected to said actuating member so that reciprocable movement of said actuating member pivotally moves said clamp arm with respect to said end-effector; and
   an annular support member mounted on said waveguide at a distal-most node thereof for resisting bending moments created during clamping of tissue against said end-effector by said clamp arm, and for sealing the region between said waveguide and said relatively reciprocable actuating member.

2. An ultrasonic surgical clamp apparatus in accordance with claim 1, wherein
   said support member includes a support portion having a generally cylindrical outer support surface, and a sealing portion having a pair of converging surfaces which converge to define a peripheral sealing region which in a non-compressed state is spaced radially outwardly of said outer support surface.

3. An ultrasonic surgical clamp apparatus in accordance with claim 2, wherein
   said sealing portion of said support member is spaced axially from said support portion.

4. An ultrasonic surgical clamp apparatus in accordance with claim 2 wherein
   said sealing portion of said support member is positioned medially of said support portion.

5. An ultrasonic surgical clamp apparatus in accordance with claim 2, wherein
   said waveguide includes a lug portion at said distal-most node having an outer cylindrical surface having a diameter greater than portions of said waveguide adjacent to said lug portion, said support portion of said support member being positioned on and flanking said lug portion of said waveguide to maintain said support member in position on said waveguide attendant to relative reciprocation of said actuating member.

6. An ultrasonic surgical clamp apparatus in accordance with claim 5, wherein
   said sealing portion of said support member is positioned medially of said support portion, and in substantial alignment with said lug portion of said waveguide.

7. An ultrasonic surgical clamp apparatus in accordance with claim 1, wherein
   a thinnest region of said support portion has a thickness of about 0.003–0.005 inches.

8. An ultrasonic surgical clamp apparatus comprising:
   a housing;
   an outer tubular sheath having a proximal end joined to said housing, and a distal end,
   an inner actuating member reciprocably positioned within said outer tubular sheath;
   an ultrasonic waveguide positioned within said inner tubular actuating member and having an end-effector extending distally of said distal end of said outer tubular sheath, said actuating member being reciprocable relative to said waveguide;
   a clamp arm pivotally mounted on said distal end of said outer tubular sheath for pivotal movement with respect to said end-effector for clamping tissue between said clamp arm and said end-effector, said clamp arm being operatively connected to said actuating member so that reciprocable movement of said actuating member pivotally moves said clamp arm with respect to said end-effector; and
   an annular support member mounted on said waveguide at a distal-most node thereof for acoustically isolating said waveguide from said actuating member, said support member comprising elastomeric material and including a support portion positioned between said waveguide and actuating member for resisting bending moments created during clamping of tissue against said end-effector by said clamp arm, said support member further including a sealing portion spaced axially from said support portion for sealing the region between said waveguide and said relatively reciprocable actuating member.

9. An ultrasonic surgical clamp apparatus in accordance with claim 8, wherein
   said support member includes a support portion having a generally cylindrical outer support surface, and a sealing portion having a pair of converging surfaces which converge to define a peripheral sealing region which, in a non-compressed state, is spaced radially outwardly of said outer support surface.

10. An ultrasonic surgical clamp apparatus in accordance with claim 8, wherein
    said sealing portion of said support member is spaced distally of said support portion.

11. An ultrasonic surgical clamp apparatus in accordance with claim 8, wherein said sealing portion of said support member is spaced proximally of said support portion.

12. An ultrasonic surgical clamp apparatus in accordance with claim 8, wherein said waveguide includes a lug portion at said distal-most node having an outer cylindrical surface having a diameter greater than portions of said waveguide adjacent to said lug portion, said support portion of said support member being positioned on and flanking said lug portion of said waveguide to maintain said support member in position on said waveguide attendant to relative reciprocation of said actuating member.

13. An ultrasonic surgical clamp apparatus in accordance with claim 8, wherein said outer tubular sheath has an outside diameter less than about 6 mm.

14. An ultrasonic surgical clamp apparatus in accordance with claim 7 wherein said support member defines an annular recess positioned intermediate said support portion and said sealing portion for accommodating deflection of said sealing portion attendant to relative reciprocation of said actuating member.

* * * * *